United States Patent [19]

Amano et al.

[11] Patent Number: 4,459,425

[45] Date of Patent: Jul. 10, 1984

[54] 3-LEVO-MENTHOXYPROPANE-1,2-DIOL

[75] Inventors: Akira Amano, Yokohama; Michio Moroe, Mitaka; Toshio Yoshida, Yokohama, all of Japan

[73] Assignee: Takasago Perfumery Co., Ltd., Tokyo, Japan

[21] Appl. No.: 411,449

[22] Filed: Aug. 25, 1982

[30] Foreign Application Priority Data

Nov. 20, 1981 [JP] Japan .................. 56-185211

[51] Int. Cl.³ ........................... C07C 43/196
[52] U.S. Cl. .......................... 568/666; 568/670; 424/57; 424/56; 426/3; 426/101; 426/660
[58] Field of Search .................. 568/670, 666

[56] References Cited

FOREIGN PATENT DOCUMENTS 2203947  8/1972  Fed. Rep. of Germany ...... 568/670
2127010  10/1973  France .
1315626  5/1973  United Kingdom .
1353381  5/1974  United Kingdom .

Primary Examiner—Bernard Helfin
Attorney, Agent, or Firm—Frishauf, Holtz, Goodman & Woodward

[57] ABSTRACT 3-l-Menthoxypropane-1,2-diol having the formula:

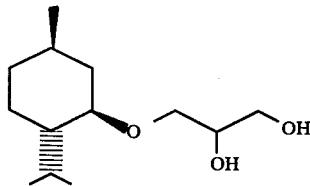

1 Claim, 3 Drawing Figures

3-LEVO-MENTHOXYPROPANE-1,2-DIOL

BACKGROUND OF THE INVENTION

1. Field of the Invention

The present invention provides the novel compound 3-l-menthoxypropane-1,2-diol which has a physiological cooling effect.

2. Description of the Prior Art

Various compounds having cooling activity are known which, when rubbed on or contacted with the skin of human body or the mucous membranes, especially those of the mouth, nose and throat, produce a cold feeling. A typical example of such compounds is menthol. The cooling activity of menthol is ascribed not to its latent heat of evaporation, but to its direct irritant action of thermal sensitive receptors at the terminals of nerves of the human body which in turn irritates the central nerve system, producing a cold sensation.

Menthol has many uses as a compound having a physiological cooling effect, for example, it is widely used in foodstuffs, drinks, dentrifrice, gargles, cosmetics, abrasives, lotions, etc., and additionally, as an additive for tobacco. Menthol rapidly dissipates in air because of its high volatility and, therefore, its effect is not sustained over a long period of time. Furthermore, since it has a strong peppermint odor, it is not desirable for some uses. It has therefore been desired to overcome the foregoing problems of menthol.

In addition to menthol, 3-substituted-p-menthanes (Japanese Patent Application Laid-Open Nos. 16647/1972 and 16649/1972), N-substituted-p-menthane-3-carboxamides (Japanese Patent Application Laid-Open No. 16648/1972), are disclosed as compounds having a physiological cooling effect.

THE INVENTION

It has been discovered that 3-l-menthoxypropane-1,2-diol having the formula (I), which is a mono-glycerin derivative of l-menthol, has excellent cooling activity.

The present invention provides 3-l-menthoxypropane-1,2-diol represented by the formula (I):

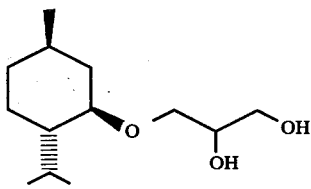

(I)

Figure 1:
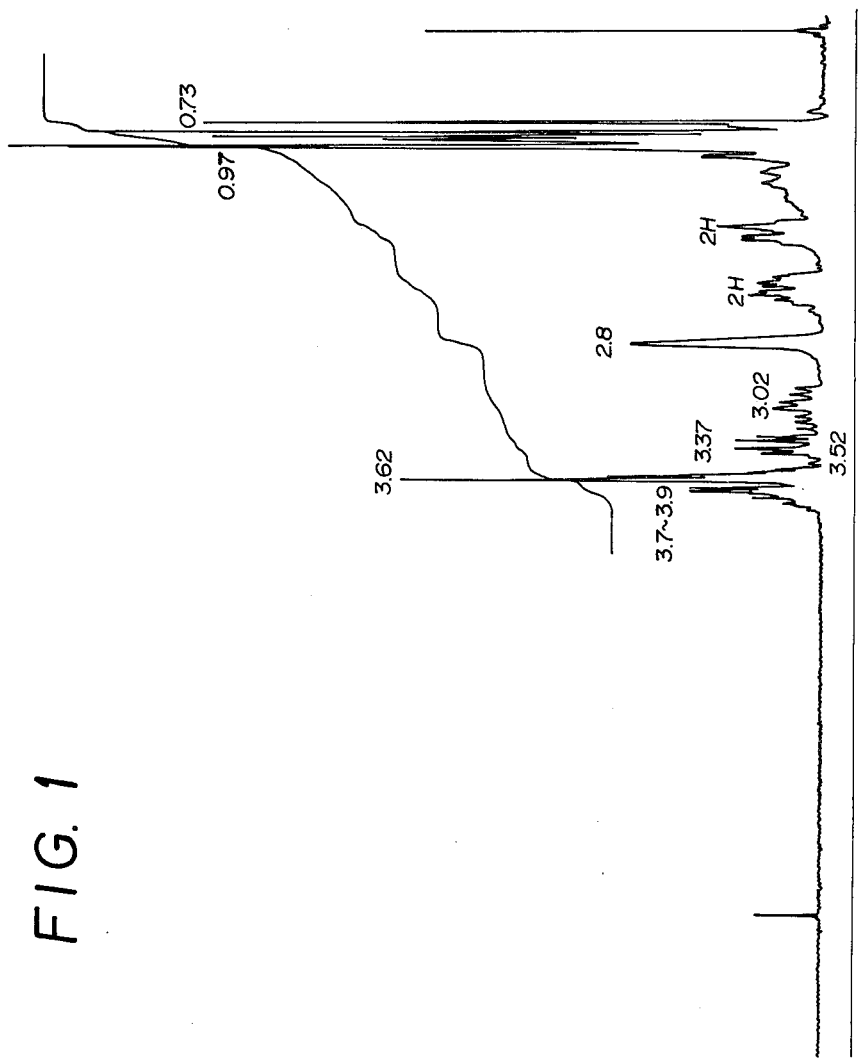
FIG. 1 is a hydrogen nuclear magnetic resonance spectrum.
Figure 2:
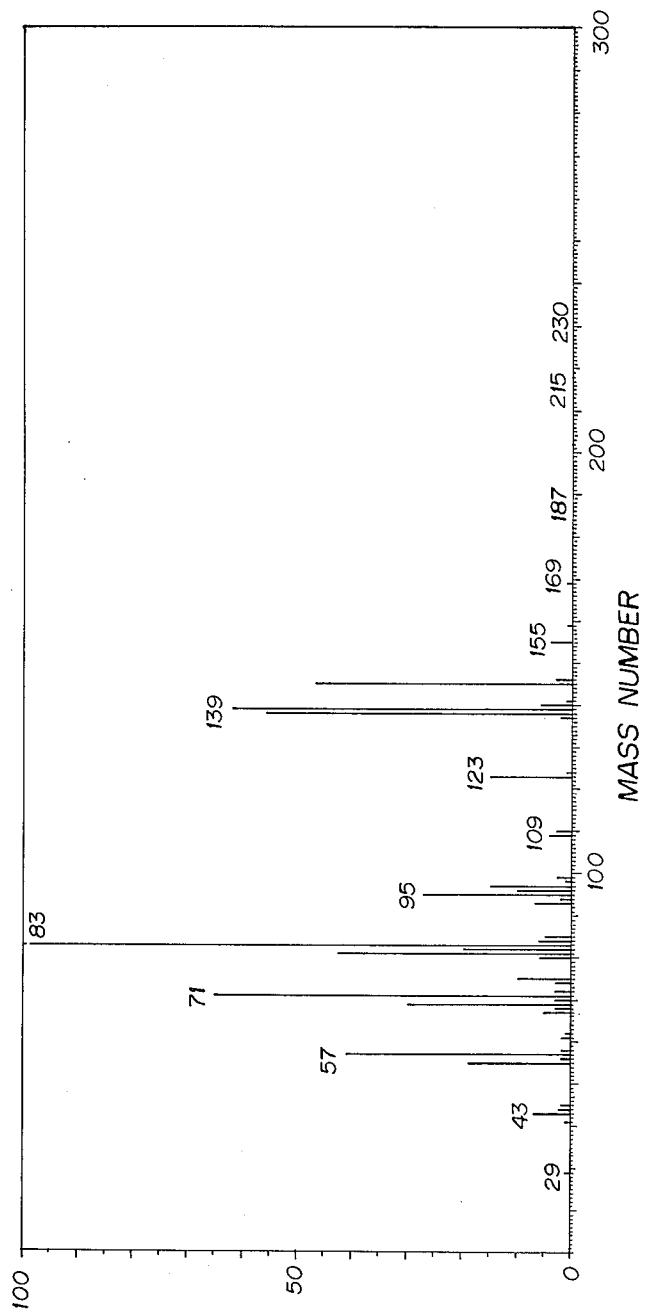
FIG. 2 is a mass spectrum.
Figure 3:
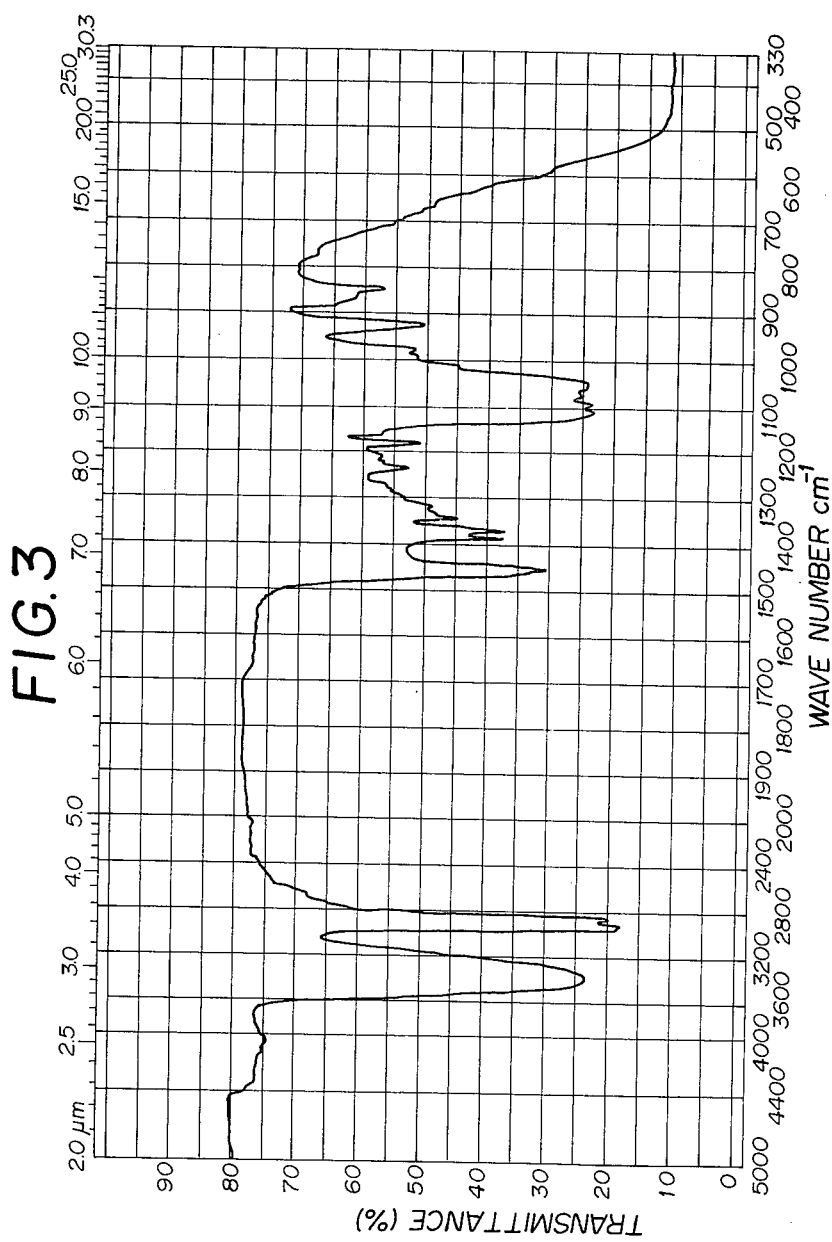
FIG. 3 is an infrared absorption spectrum of the compound of this invention, respectively.

DETAILED DESCRIPTION OF THE INVENTION 3-l-Menthoxypropane-1,2-diol is synthesized from l-methanol represented by the formula (V) according to the following reaction:

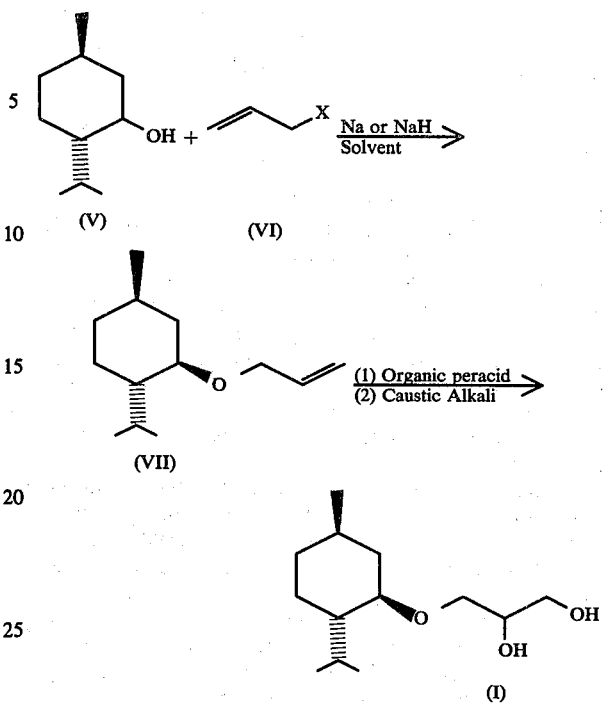

Prior to the reaction between menthol and allyl halide (Formula (VI)), the menthol is first converted into the corresponding alkali salt.

l-Menthol and metallic sodium or sodium hydride are introduced into a solvent, e.g., toluene or xylene, and heated. When the temperature reaches 100° C. or higher, the reaction starts and generation of hydrogen gas occurs. After confirming that the generation of hydrogen has stopped, the mixture is further heated at the reflux temperature of the solvent to complete the reaction.

Allyl halide, e.g., allyl chloride or allyl bromide, is then added to the reaction mixture in small portions. As the reaction proceeds, sodium halide deposits and the reaction solution becomes slurry-like. After the reaction is completed, the reaction solution is cooled, and after addition of water, the resulting mixture was stirred. Then, a solvent, e.g., benzene, toluene, ether, hexane, or petroleum ether, is added thereto. The organic layer is separated and washed with saturated saline water. After the solvent is recovered, the residue is distilled under reduced pressure to obtain 3-l-menthoxypropane-1-ene (Formula (VII)). Yield is 90% or more based on the menthol.

The 3-l-menthoxypropane-1-ene (VII) is then oxidized into the corresponding oxide by the use of an organic peracid. The oxide is hydrolyzed to form the desired 3-l-methoxypropane-1,2-diol. That is, an organic acid, e.g., formic acid or acetic acid, and aqueous hydrogen peroxide are mixed with 3-l-menthoxypropane-1-ene and gradually heated carefully while stirring. The organic acid and the hydrogen peroxide react, forming an organic peracid which participates in the oxidation reaction. The reaction is exothermic, and rapid heating should be avoided. When the temperature of the reaction solution reaches near 50° C., the heating is stopped. It is, thereafter, necessary for the temperature of the reaction solution to be maintained at about 70° C. by external cooling to prevent a further temperature increase caused by the heat of reaction. If the temperature of the reaction solution is excessively high, the organic peracid decomposes before it participates in the oxidation reaction, resulting in a reduction in yield.

After the reaction is completed, a solvent, e.g., benzene, toluene, xylene, or petroleum ether, is added to perform the extraction. The extracted liquid is washed with water. Upon recovery of the solvent by distillation, a crude oxide in the form of an organic acid ester is produced. The crude oxide thus formed is mixed with an about 20% aqueous solution of caustic soda, for example, and is hydrolyzed by boiling for about 1 hour to produce the desired 3-l-menthoxypropane-1,2-diol.

The resulting 3-l-menthoxypropane-1,2-diol is then extracted with a solvent, e.g., dichloroethane, methylene chloride, or chloroform, by the usual technique, washed with water, dried, and, thereafter, is freed of the solvent and distilled under reduced pressure to produce 3-l-menthoxypropane.

As described above, the compound of the invention, 3-l-menthoxypropane-1,2-diol, can be prepared from an easily available starting material and auxiliary agents by a simplified procedure in limited stages. The compound of the invention is a liquid which is of low volatility and is almost odorless. Since the compound of the invention is not limited by inadequate volatility and odor characteristics, it is expected to find many uses as a cooling agent in addition to those exemplified here.

The invention is described in more detail by reference to the following examples.

EXAMPLES

Preparation of 3-l-Menthoxypropane-1-ene

Toluene (280 milliliters), 93.6 grams (0.6 mole) of l-menthol, and 27 grams (0.709 mole) of sodium hydride (63% dispersion in paraffin) were placed in a 500-ml flask equipped with a reflux condenser and heated. When the temperature reached 100° C., the reaction started and hydrogen gas was generated. The reaction mixture was maintained at the reflux temperature of toluene for 3 hours to form the sodium salt of l-menthol. The completion of the reaction was confirmed by examining whether or not the generation of hydrogen stopped.

Then, 65 grams (0.85 mole) of allyl chloride was added dropwise to the reaction solution over a period of 30 minutes while maintaining the reaction solution in the state that it was gently refluxed, and the reaction was further continued for 1 hour. Sodium chloride deposited and the reaction solution became slurry-like. After the reaction was completed, the reaction solution was cooled and, after addition of water, the organic layer was extracted with toluene. The organic layer thus extracted was washed with saturated saline water, dried over anhydrous magnesium sulfate, freed of toluene by distillation, and distilled under reduced pressure to produce 106.7 g of 3-l-menthoxypropane-1-ene having a boiling point of 59-60 degrees centigrade per 1 millimeter mercury (°C./1 mmHg). The purity was 99.3% and yield was 91.7%.

Preparation of 3-l-Menthoxypropane-1,2-diol

Formic acid (280 grams), 70 grams (0.618 mole) of a 30% aqueous solution of hydrogen peroxide, and 80 grams (0.412 mole) of the 3-l-menthoxypropane-1-ene which was produced in the preceeding preparation example were mixed and gradually heated with stirring. When the temperature of the reaction solution reached 50° C., heating was stopped. Thereafter, since the liquid temperature raised by the heat of reaction, when it reached 65° C., the reaction solution was cooled by means of an ice water bath and, thereafter, while carefully keeping the reaction temperature lower than 70° C., the reaction was continued for 3 hours. At the end of the time, the reaction solution was cooled to room temperature and, after addition of water, toluene was added to perform extraction. The extract was washed with water and then, was freed of the solvent to produce 110 grams of a crude oxide.

The crude oxide thus produced was mixed with 200 grams of a 20% aqueous solution of caustic soda and held at reflux for one hour. The organic layer was extracted with chloroform, washed with water, and dried over anhydrous magnesium sulfate. Upon recovery of the solvent, 90 grams of a crude product was produced. The crude product was purified by vacuum distillation to form 69 grams of 3-l-menthoxypropane-1,2-diol having a boiling point of 121-125 degrees centigrade per 0.25 millimeter mercury (°C./0.25 mmHg). The purity was 98%. Its properties and instrumental analysis values are as follows:

Specific density $d_{25}^{25}$ 1.004
Refractive index $n_D^{25}$ 1.4727
Specific rotation $[\alpha]_D^{25}$ −77.2°
Infra-red (IR, NaCl liquid membrane, cm$^{-1}$) 3380, 2960, 2930, 2870, 1455, 1388, 1370, 1345, 1320, 1240, 1183, 1110, 1090, 1070, 1055, 1045, 978, 923, 845
Mass spectrum (MS, m/e) 230(M+), 215, 201, 169, 155, 145, 139, 138, 123, 97, 95, 83(P), 82, 81, 71, 69, 57, 55
Nuclear magnetic resonance (NMR, CDCl$_3$, ppm)
0.73-1.2 (12H; 7—C$\underline{H}_3$, 9—C$\underline{H}_3$, 10—C$\underline{H}_3$, 5—H$_{ax}$, 6—H$_{ax}$, 1—H of menthane),
1.05-1.5 (2H; 2—H$_{ax}$, 4—H of menthane),
1.55-1.7 (2H; 5—H$_{eq}$, 6—H$_{eq}$ of menthane),
1.96-2.3 (2H; 2—H$_{eq}$, 8—H of menthane),
2.56 (2H; two O—H),
3.02 (1H, m; 3—H of menthane),
3.37 (1H, quar; 3—H of propane),
3.52-3.9 (4H, m; 3—H, 1—H$_2$, 2—H of propane)

Applied Example 1

Tooth Powder

|  | parts by weight |
|---|---|
| Light calcium carbonate | 500 |
| Heavy calcium carbonate | 350 |
| Sodium lauryl sulfate | 10 |
| Saccharin | 1 |
| Tooth paste flavor X-9135 (flavor for tooth paste, manufactured by Takasago Perfumery Co., Ltd.) | 8 |
| 3-l-Menthoxypropane-1,2-diol (compound of the invention as prepared above Example) | 2 |
| Water to make | 1,000 |

The above ingredients were mixed in a blender to produce a tooth powder. This tooth powder had a refreshing effect, and a refreshing feeling having no bitter taste was retained in the mouth over a long period of time.

Applied Example 2

Wet Tooth Powder

| | parts by weight |
|---|---|
| Potassium hydrogenphosphate | 300 |
| Water-insoluble sodium metaphosphate | 350 |
| Sodium lauroylsarcosinate | 15 |
| Glycerin | 100 |
| Saccharin | 1.5 |
| Tooth paste flavor X-9135 (flavor manufactured by Takasago Perfumery Co., Ltd.) | 8 |
| 3-l-Menthoxypropane-1,2-diol (compound of the invention as prepared above Example) | 2 |
| Water to make | 1,000 |

The above ingredients were mixed in a blender to form a wet tooth powder. This wet tooth powder has a refreshing effect, and a refreshing feeling having no bitter taste was retained in the mouth over a long period of time.

Applied Example 3

Tooth Paste

| | parts by weight |
|---|---|
| Potassium hydrogenphosphate | 500 |
| Carboxymethyl cellulose | 10 |
| Sodium lauryl sulfate | 20 |
| Glycerin | 250 |
| Saccharin | 2 |
| Tooth paste flavor X-9135 (flavor manufactured by Takasago Perfumery Co., Ltd.) | 8 |
| 3-l-Menthoxypropane-1,2-diol (compound of the invention as prepared above Example) | 2 |
| Water to fill up | 1,000 |

The above ingredients were mixed in a blender to form a tooth paste. This tooth paste has a refreshing effect, and a refreshing feeling having no bitter taste was retained in the mouth over a long period of time.

Applied Example 4

Chewing Gum

| | parts by weight |
|---|---|
| Gum base | 230 |
| Powdery sugar | 480 |
| Glucose | 160 |
| Starch syrup | 117 |
| Plasticizer | 1 |
| Cola flavor E-7002 (flavor manufactured by Takasago Perfumery Co., Ltd.) | 10 |
| 3-l-Menthoxypropane-1,2-diol (compound of the invention as prepared above Example) | 2 |
| (total) | 1,000 |

The above ingredients were mixed in a kneader to prepare a chewing gum. This chewing gum was compared with a chewing gum to which the compound of the invention was not added, with the results that the addition of the compound of the invention reduced the stiff flavor of Cola Flavor E-7002, producing a mellow feeling, and, furthermore, provided a feeling which was felt in the mouth when drinking cider i.e., a sparkling feeling, and that a refreshing feeling having no bitter taste was retained in the mouth over a long period of time.

Applied Example 5

Sherbet

| | parts by weight |
|---|---|
| First-class sugar | 200 |
| Powdered starch syrup | 40 |
| Stabilizer | 3 |
| Caramel | suitable amount |
| Cola flavor E-7003 (flavor manufactured by Takasago Perfumery Co., Ltd.) | 1 |
| 3-l-Menthoxypropane-1,2-diol (compound of the invention as prepared above Example) | 0.05 |
| Water to make | 1,000 |

The above ingredients were mixed and placed in a freezer to prepare a sherbet. Comparison of the sherbet with a sherbet to which the compound of the invention was not added showed that the flavor in the sherbet containing the compound of the invention gave a mild and mellow feeling. A short period of time after being eaten, a considerable part of the refreshing effect in the mouth was retained.

Applied Example 6

Hard Candy

| | parts by weight |
|---|---|
| Granulated sugar | 600 |
| Starch syrup (water content 20%) | 500 |
| Water | 250 |
| (total) | 1,350 |

The above ingredients were mixed and then heated to 150° C. at ambient pressure by the conventional procedure to form a hard candy.

In the preparation of the hard candy, prior to the solidification of the ingredients by cooling, 0.1% of a cider flavor (Cider Flavor E-7004, manufactured by Takasago Perfumery Co., Ltd.) and 0.005% of the compound of the invention as prepared above Example, 3-l-menthoxypropane-1,2-diol, were added.

The thus-prepared hard candy was compared with a candy to which the compound of the invention was not added, with the results that the addition of the compound of the invention reduced the stiffness of the cider flavor which was felt when eating the comparative hard candy, providing a mild and mellow flavor and, furthermore, produced a considerable refreshing feeling similar to that felt when drinking sparkling drinks such as cider, i.e., a refreshing feeling associated with a sparkling feeling.

The compound of the present invention has unique properties which are not shared with other compounds which also contain the p-menthane skeleton in their molecular structure, including the 3-substituted-p-menthanes, N-substituted-p-menthane-3-carboxamides, and para-menthane-diols referred to hereinbefore.

3,5,5-Trimethylcyclohexanol monoglycerin ether represented by the formula (II) was synthesized and tested:

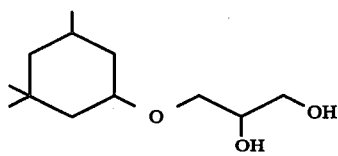

(II)

This compound tasted very bitter, and its cooling activity was very poor. Another compound was 3-l-menthoxybutane-2,3-diol represented by the formula (III):

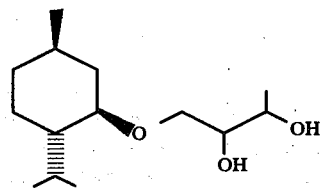

(III)

which contained a methyl group at the 1-position of the propane chain of the compound of the invention represented by the formula (I). This compound tasted very bitter, although it had cooling activity. In addition, the compound described in Japanese Patent Application Laid-Open No. 16649/1972, represented by the formula IV):

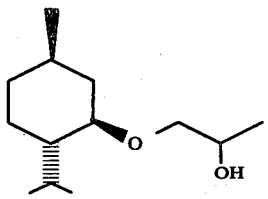

(IV)

was synthesized, and its properties were examined. It was found that the compound had dry grass-like odor and a bitter taste, and that its cooling activity was very poor.

It has also been found that the aliphatic acid esters, ketals, and acetals of the compound of the invention do not have cooling activity.

What is claimed is:

1. 3-l-Menthoxypropane-1,2-diol having the formula:

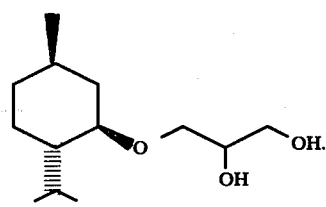

* * * * *